United States Patent
Garrigue et al.

(10) Patent No.: US 11,458,296 B2
(45) Date of Patent: Oct. 4, 2022

(54) VENTRICULAR ASSISTANCE ASSEMBLY WITH STABILIZED CARDIAC PUMP

(71) Applicant: FINEHEART, Pessac (FR)

(72) Inventors: Stéphane Garrigue, Begles (FR); Arnaud Mascarell, Montbazon (FR)

(73) Assignee: FINEHEART

( * ) Notice: Subject to any disclaimer, the term of this patent is extended or adjusted under 35 U.S.C. 154(b) by 153 days.

(21) Appl. No.: 16/965,487

(22) PCT Filed: Jan. 28, 2019

(86) PCT No.: PCT/FR2019/050176
§ 371 (c)(1),
(2) Date: Jul. 28, 2020

(87) PCT Pub. No.: WO2019/145657
PCT Pub. Date: Aug. 1, 2019

(65) Prior Publication Data
US 2021/0052792 A1    Feb. 25, 2021

(30) Foreign Application Priority Data
Jan. 29, 2018 (FR) ...................................... 1850699

(51) Int. Cl.
*A61M 60/174* (2021.01)
*A61M 60/148* (2021.01)
(Continued)

(52) U.S. Cl.
CPC ........ *A61M 60/148* (2021.01); *A61M 60/857* (2021.01); *A61M 60/894* (2021.01)

(58) Field of Classification Search
CPC . A61M 60/148; A61M 60/894; A61M 60/857
(Continued)

(56) References Cited

U.S. PATENT DOCUMENTS

| 9,731,057 B2 | 8/2017 | Garrigue |
| 2010/0249489 A1 | 9/2010 | Jarvik |

(Continued)

FOREIGN PATENT DOCUMENTS

| WO | 2010010407 | 1/2010 |
| WO | 2013014339 | 1/2013 |
| WO | 2016005803 | 1/2016 |

OTHER PUBLICATIONS

International Search Report issued on International Patent Application No. PCT/FR2019/050176 dated May 13, 2019.

*Primary Examiner* — Erin M Piateski
(74) *Attorney, Agent, or Firm* — Perman & Green, LLP

(57) ABSTRACT

A ventricular assist assembly, for assisting a heart, includes an anchoring device, a cardiac pump and a stabilizing device. The anchoring device anchors a cardiac pump, is intended to be assembled with an opening in a ventricular wall of the heart, and delimits an internal passage.
The cardiac pump is intended to be attached to the anchoring device, is configured for intra-ventricular insertion into the heart, and has a distal end.
The cardiac pump extends through the internal passage into the heart when attached to the anchoring device implanted in the opening so that its distal end is placed in a ventricular chamber.
The stabilizing device stabilizes the cardiac and includes at least two elongate, biocompatible and flexible connecting members, each elongate connecting member being intended to connect a part of the cardiac pump that is positioned in the ventricular chamber to an internal wall of the ventricular chamber.

10 Claims, 2 Drawing Sheets

(51) Int. Cl.
*A61M 60/894* (2021.01)
*A61M 60/857* (2021.01)

(58) Field of Classification Search
USPC .......................................................... 600/16
See application file for complete search history.

(56) References Cited

U.S. PATENT DOCUMENTS

| | | |
|---|---|---|
| 2011/0124950 A1 | 5/2011 | Foster |
| 2014/0207232 A1* | 7/2014 | Garrigue ............ A61M 60/422 |
| | | 623/3.13 |
| 2016/0000983 A1 | 1/2016 | Mohl et al. |
| 2017/0197019 A1* | 7/2017 | Tuseth ................ A61M 60/122 |

* cited by examiner

VENTRICULAR ASSISTANCE ASSEMBLY WITH STABILIZED CARDIAC PUMP

CROSS REFERENCE TO RELATED APPLICATIONS

This application is a National Stage of International Application No. PCT/FR2019/050176, having an International Filing Date of 28 Jan. 2019, which designated the United States of America, and which International Application was published under PCT Article 21(2) as WO Publication No. 2019/145657 A1, which claims priority from and the benefit of French Patent Application No. 1850699, filed on 29 Jan. 2018, the disclosures of which are incorporated herein by reference in their entireties.

BACKGROUND

1. Field

The present disclosure relates to a ventricular assist assembly comprising a device for stabilizing a cardiac pump so as to maintain that part thereof that is placed in a ventricle of a beating heart centered on the corresponding valve.

2. Brief Description of Related Developments

Cardiac insufficiency (CI) is a pathological condition in which the heart of a patient is unable to supply the rate of blood flow necessary to meet the metabolic needs of the organism.

It is known practice, in order to treat cardiac insufficiency, to implant a ventricular assist device (VAD), which is an artificial cardiac pump.

This mechanical pump does not replace the heart, which continues to function, but provides assistance to the weakened ventricle so as to increase the rate of blood flow in a way suited to the needs of the individual.

This assistance may be temporary, while awaiting an available graft in order to perform a heart transplant.

However, it is found that a significant proportion of patients do not receive such a graft, either because they are unsuitable candidates for such a transplants, for example because of severe cardiac insufficiency, or because no suitable graft is available for these patients.

In that case, ventricular assistance is used as the intended solution, which means to say that the artificial cardiac pump is implanted for the long-term.

These cardiac pumps are therefore the subject of intense research aimed at improving the survival and quality of life of patients presenting with cardiac insufficiency.

Numerous advances have been made over recent years and ventricular assist devices that are more compact, quieter, and offer lengthened service lives, are now known.

The implantable cardiac pumps of the prior art are therefore typically equipped with an integrated electric motor in order to operate them, the rotational speed of the pump providing the force necessary to cause the blood to circulate from the weakened ventricle to the circulatory system.

The controller and the power source for the cardiac pump are typically placed outside the patient's body. A percutaneous line through the abdomen therefore provides the connection between the pump attached to the wall of the ventricle and these external elements.

Patent application WO2013014339 A1 in the name of the present applicant company describes an electric cardiac pump that is particularly reliable and easy to install and the control unit and electric battery of which are implanted.

Although this represents undeniable progress in terms of the quality of life of a patient suffering from cardiac insufficiency, the operation of these cardiac pumps still leaves room for improvement.

Specifically, such cardiac pumps typically have a pump casing or body the distal end of which is formed by a small-diameter duct through which the blood is ejected toward the corresponding heart valve, generally the aortic valve.

Now, as a result not only of the daily activities performed by a patient equipped with such a ventricular assist device, but also of the knocks that this patient may experience in their activities, it is found that the distal end of the cardiac pump is liable to shift to such a point that it is no longer positioned facing the corresponding valve, notably the aortic valve.

Not only is the rate of flow of blood passing through this valve therefore reduced, but the distal end of the pump may also, in extremis, come into contact with a wall of the heart and cause the formation of a thrombus, or blood clot, that is particular dangerous to the patient.

There is therefore a pressing need for a device that makes it possible to stabilize the position of that part of a cardiac pump that is placed in a ventricle of a beating heart in order to maintain it centered on the corresponding valve.

SUMMARY

The present disclosure seeks to alleviate the disadvantages of the prior art and to meet the abovementioned requirements, by proposing a device for maintaining the free end, or blood-ejection duct, of an implantable cardiac pump that is intended for intraventricular insertion, which is simple in its design and in its mode of operation, biocompatible, and particularly mechanically reliable.

The present disclosure notably targets such a device for stabilizing the free end of a cardiac pump, allowing this free end to be maintained firmly in a position that is centered on the corresponding valve of the human heart.

Another object of the present disclosure is such a stabilizing device that allows the practitioner to operate on the cardiac pump from outside the ventricle, for example in order to replace the pump or one of the components thereof.

The present disclosure also targets a method for stabilizing a cardiac pump intended to assist a human heart which is simple and allows operations on the cardiac pump without the need for major surgical intervention.

To this end, the disclosure relates to a ventricular assist assembly for assisting a heart, said assembly comprising:
  an anchoring device for anchoring a cardiac pump, which device is intended to be assembled with an opening in a ventricular wall of said heart, said anchoring device delimiting an internal passage,
  a cardiac pump intended to be attached to said anchoring device, said cardiac pump being configured for intraventricular insertion into said heart, said cardiac pump having a distal end,
  said pump extending through the internal passage of the anchoring device into this heart when attached to said anchoring device implanted in said opening so that its distal end is placed in a ventricular chamber,
  a stabilizing device for stabilizing this cardiac pump, comprising at least two elongate, biocompatible and flexible connecting members, each elongate connecting member being intended to connect a part of said cardiac pump that is positioned in said ventricular chamber to an internal wall of said ventricular chamber.

Because this cardiac pump is anchored in the wall of the heart with intraventricular insertion, and because its blood-ejection end or duct is stabilized by the stabilizing device in an optimal position with respect to the corresponding valve, the patient can now move around actively without any risk.

The free end of the cardiac pump thus remains centered on the corresponding valve, notably the aortic valve.

In the context of the present disclosure, the term "proximal" means the position closest to the healthcare professional, or to the practitioner, while the term "distal" is to be understood here as meaning the most distant from this professional. In other words, the distal end of an elongate cable or a rod is the end which is the first end engaged into a cable passageway of the cardiac pump while the proximal end would be the last end engaged.

In various particular embodiments of this assembly, each of which has its own particular advantages and which can be combined in numerous possible technical combinations:

for each elongate connecting member, said assembly comprises an attachment element so as to anchor said connecting member in said internal wall
Preferably, this attachment element is an anchoring screw axially extending said elongate connecting member and placed at the distal end thereof,
each elongate connecting member is chosen from the group comprising an elongate cable, a filament, a chord, a rod and combinations of these elements,
said assembly also comprises a ring or a collar intended to surround the distal end of said cardiac pump, at least some of said elongate connecting members being secured by one of their ends to this ring or, respectively, to this collar.

Advantageously, with these elongate connecting members being secured to the ring or to the collar, the assembly formed by said ring or said collar and said connecting members is made from a shape memory material so that, when introduced into the chamber, this assembly transitions from a non-deployed configuration to a deployed configuration in which the free ends of the connecting members come to bear against the internal walls of said ventricular chamber The material used may be a shape memory alloy (SMA), the most commonly used alloy being nitinol. Such a material offers the advantage of being strong and lightweight while at the same time offering this particular feature of being able to deform at a given temperature and of recovering its initial shape, a non-deformed shape, when its temperature reaches a temperature higher than a temperature known as the transformation temperature.

With each elongate connecting member being an elongate cable or a rod, said cardiac pump comprises cable passageways configured to each allow the insertion of a corresponding elongate cable or rod, from the outside of the heart toward the inside of said ventricular chamber when said pump is attached to the anchoring device.

Preferably, the body of each elongate cable or rod is configured to exhibit enough torsional stiffness to transmit along its entire length a rotational movement that is imparted from a proximal end of this cable or of this rod.

Advantageously, the cable passageways extend from the proximal end of said cardiac pump as far as a part of said pump that is intended to be placed inside said chamber when said pump is attached to the anchoring device secured to said opening.

Purely by way of illustration, these passageways may open to the distal end of said cardiac pump.

Thus, and extremely advantageously, the stabilizing device is fully accessible from outside the ventricle, and the practitioner can manipulate the elongate cables or rods from outside the heart, with the cardiac pump in its position assembled with its anchoring ring.

The cardiac pump is thus easily interchangeable and simpler to maintain without the need for major surgery.

As a result, the cardiac pump remains particularly easy to replace in the event of a component breaking down or wearing out.

Preferably, at least part of at least one of said passageways is positioned in the thickness of the lateral wall delimiting the pump body and/or is delimited by a hollow and elongate element projecting from the pump body, namely placed on the outside of the pump body.

In the latter case, and by way of example, this may be an element having a U-shaped or half-round-shaped cross section.

Of course, the anchoring device may be configured to allow the insertion and passage of a cardiac pump of which the pump body has one or more projecting elements while at the same time providing the necessary sealing. For example, the interior wall of the anchoring device delimiting the orifice for the passage of the pump body may have recesses the shapes of which complement those of the elements projecting from the pump body.

According to one particularly advantageous aspect, each passageway comprises a nonreturn valve in order to seal same.

Said pump is a propulsive cardiac pump.

The present invention also relates to a ventricular assist system for assisting a heart, comprising a ventricular assist assembly as described hereinabove.

According to the disclosure,
the anchoring device of said cardiac pump being assembled with an opening made in the ventricular wall of said heart,
said pump being connected to said anchoring device in such a way that a part of said pump passing through an orifice delimited by said anchoring device has its proximal end positioned outside said heart and its distal end placed in a ventricular chamber of said heart,
said pump having elongate-cable passageways configured to each allow the insertion of an elongate and flexible cable or a rod from outside the heart toward the inside of said chamber,
a first elongate cable, or a first rod, passing through a first of said passageways placed on a first edge of said pump has its distal end anchored into the tissue of a septum of this heart and a second elongate cable, or a second rod, passing through a second of said passageways placed on the edge of said pump opposite to the edge receiving said first passageway has its distal end anchored in the tissue of a wall internal to said ventricular chamber and contiguous with the aortic valve so that the distal end of said cardiac pump is stabilized in position in said ventricular chamber.

Of course, every attempt will be made to anchor said elongate and flexible cables, or rods, in the ventricular chamber in such a way that the distal end of said pump is positioned facing the aortic valve and centered thereon.

Likewise, that part of the cardiac pump that is placed in the chamber may be connected by more than two elongate cables and/or rods.

The present disclosure also relates to a method for stabilizing a cardiac pump intended to assist a heart, said pump having a distal end and a proximal end, in which method, after having assembled an anchoring device for anchoring said cardiac pump with an opening made in the ventricular wall of said heart, and having connected said pump to said anchoring device so that a part of said pump that passes through an orifice delimited by said anchoring device has its proximal end positioned outside said heart and its distal end positioned in a ventricular chamber.

According to the disclosure, with said pump having passageways for elongate and flexible cables, which passageways are configured to allow the insertion of such cables, or of rods, from outside the heart toward the inside of said chamber when said pump is attached to the anchoring device, the following steps are performed:

a first elongate cable, or a first rod, is introduced from outside the heart into a first passageway until the free end of said first cable, or of the first rod, emerges into the ventricular chamber, then said free end is brought closer to a septum of this heart and attached in said septum, a second elongate cable or a second rod is introduced, from outside the heart, into a second passageway until the free end of said second cable, or of the second rod, emerges in the ventricular chamber, then said free end is brought closer to an internal wall of said ventricular chamber and contiguous with the aortic valve then attached to this wall, and then possibly said elongate cables are tensioned in order to stabilize the free end of said cardiac pump in said chamber.

By way of example, this tensioning may be achieved by pulling on the elongate cables or on the rods from the side of the proximal end of said cardiac pump.

Of course, every attempt will be made to position said elongate cables or rods in the ventricular chamber in such a way that the distal end of said pump is positioned facing the aortic valve and centered thereon.

According to one aspect of this method, at least a third elongate cable, or a third rod, is introduced into a corresponding passageway of the cardiac pump until the free end of said third cable, or of the third rod, emerges into the ventricular chamber, then said free end is brought closer to a wall internal to said ventricular chamber and is attached in said wall.

This introduction of the cables or of the rods can be performed axially with respect to the pump body or they may be introduced laterally.

As a preference, each passageway is configured to collaborate with its elongate cable to provide sealing, once the cable is in position. Thus, and according to another aspect of this method, each passageway comprises a non-return valve in order to seal same prior to the introduction of an elongate cable or of a rod.

Advantageously, with each elongate cable having a piercing spike at its free end, the tissue of each wall is pierced in order to anchor the corresponding elongate cable.

With such a stabilizing device, the practitioner may advantageously orient the free end of the elongate and flexible cable, or of the rod, toward a wall of the ventricular chamber, until it makes contact with this wall, whereupon they can then anchor the free end thereof by screwing this free end into the tissue of the wall.

According to yet another aspect of this method, said passageways extend from the proximal end of said pump, on the outside of the heart, as far as a part of said pump that is intended to be implanted inside said chamber when said pump is attached to the anchoring device.

Thus, the manipulation of the elongate cables and/or of the rods can be performed by the practitioner when the cardiac pump is attached to its anchoring device. This results in great ease of maintenance of the cardiac pump, which can easily be manipulated by the practitioner without the need for major surgery for the patient in order to access the stabilizing device.

Purely way of illustration, these passageways may open at the distal end of said cardiac pump.

According to yet another aspect of this method, each passageway is positioned at least partly in the thickness of the lateral wall delimiting the pump body and/or is delimited by an element projecting from the pump body, said element being hollow and elongate.

In the latter instance, it may for example be an element having a U-shaped or half-round-shaped cross section.

The anchoring device may be configured to allow the insertion and passage of a cardiac pump, the pump body of which has one or more projecting elements, while at the same time providing the necessary sealing. For example, the interior wall delimiting the orifice for the passage of the pump body may have recesses the shapes of which complement those of the elements projecting from the pump body.

BRIEF DESCRIPTION OF THE DRAWINGS

Further advantages, objects and particular features of the present disclosure will become apparent from the following description, given for nonlimiting explanatory purposes with reference to the attached drawings, in which.

DETAILED DESCRIPTION

First of all, it should be noted that the figures are not to scale.

Figure 1:
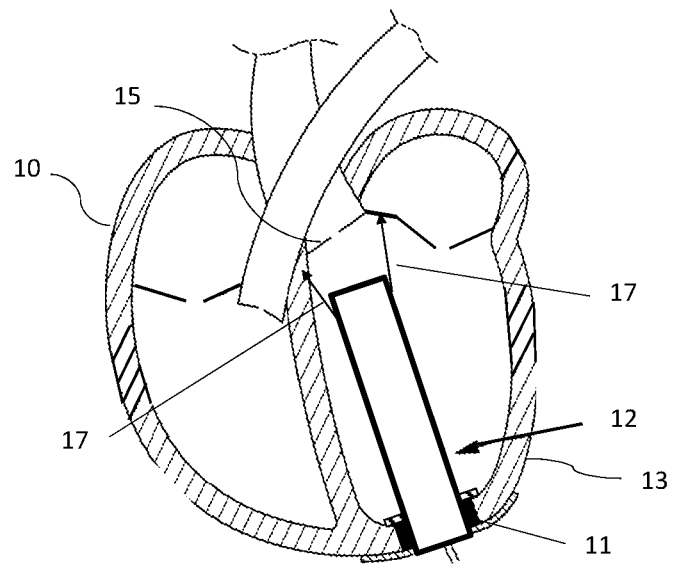
FIG. 1 schematically depicts a ventricular assist assembly for a human heart according to one particular aspect of the disclosure, the cardiac pump being inserted into the left ventricle of this heart.
Figure 2:
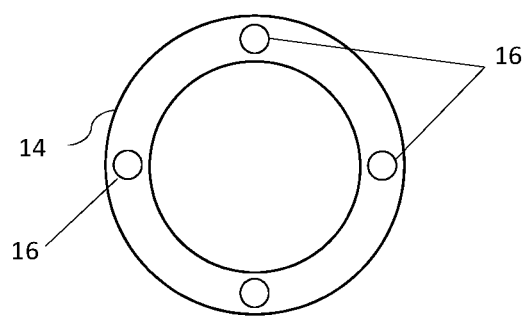
FIG. 2 is a schematic view in cross section of just the pump casing or body of the cardiac pump of FIG. 1, showing the cable passageways.
Figure 3:
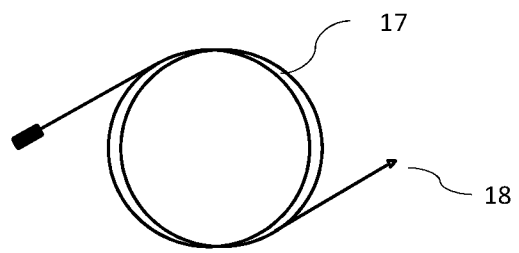
FIG. 3 shows an elongate cable used in the ventricular assist assembly of FIG. 1 and intended to be inserted into one of the cable passageways of the pump body.

FIGS. 1 to 3 schematically show a ventricular assist assembly for a human heart 10 according to one particular aspect of the present disclosure.

This assembly comprises a ring 11 for anchoring a cardiac pump 12, which is assembled with an opening made in the ventricular wall 13 of this heart 10.

This anchoring ring 11 comprises at its ends collars or flanges, which bear on each side of the ventricular wall 13 in order to permanently attach this ring 11 to the ventricular wall 13.

The collar intended to be pressed firmly against the interior surface of the ventricular wall 13 is preferably made from a shape-memory material such as nitinol, so that it can pass through the opening made in the ventricular wall 13 in a deformed state, in which it has a tubular shape or substantially tubular shape, and regain its initial shape, that of a flange, after it has been introduced into the corresponding ventricular chamber.

The anchoring ring 11 has an orifice for the passage of part of the cardiac pump 12 when it is being attached to this anchoring ring 11.

This cardiac pump 12 is additionally configured for intraventricular insertion, which means to say that the distal end of the pump body 14, or casing, is intended to be positioned in the corresponding ventricular chamber once this pump is attached to the anchoring ring 11.

Thus, because this cardiac pump 12 is connected to the anchoring ring 11, part of the pump body 14 passes through the orifice delimited by the anchoring ring 11, while the proximal end of the pump body 14 is positioned externally to, or flush with, the ventricular wall 13. The distal end is positioned in the ventricular chamber upstream of the aortic valve 15, with respect to the direction in which the blood is ejected.

The pump body 14 also defines a housing to accommodate a motor (not depicted) which is placed in the ventricular chamber and/or in the thickness of the ventricular wall 13, so as to draw in and then deliver the blood, from the bottom, into the ventricular chamber and in the direction of the aortic valve 15, through the pump body 14.

In order to stabilize the pump body 14 in the ventricular chamber, in an optimum position facing the aortic valve 15, the pump body 14 or casing has elongate-cable passageways 16 which are configured to each allow the insertion of an elongate and flexible cable 17 from outside the heart toward the inside of the ventricular chamber.

Thus, because these passageways 16 extend axially from the proximal end of the pump body as far as the distal end thereof, the elongate and flexible cables 17 can be manipulated from outside the ventricle.

FIG. 2 shows a view in cross section of just the pump body 14, which has in its thickness passageways 16 uniformly distributed around the periphery of this body.

Each passageway 16 comprises at least one sealing element (not depicted), such as a nonreturn valve, to seal the passageway prior to the insertion of an elongate and flexible cable 17.

As depicted in FIG. 1, a first elongate and flexible cable 17 passes through a first of these cable passageways 16 positioned on a first edge of said cardiac pump 12 and reemerges from this body via the distal end of the pump body 14.

The free end of this cable 17, which comprises a projecting helical screw or attachment element 18 positioned in the axial continuation of the cable and able to penetrate the tissue of a wall of the heart under the effect of a screwing motion imparted from the proximal end of the elongate cable, is anchored in the tissue of a septal wall of the left ventricle of this heart ("left septal wall").

A second elongate and flexible cable 17 passing through a second passageway 16 placed on the opposite edge of this pump 12 to the edge that accommodates the first passageway, has its distal end anchored in the tissue of a wall internal to said ventricular chamber and adjoining the aortic valve 15. By way of example, this latter wall is the aortic outflow tract.

Because these cables 17 are under tension, the cardiac pump 12 is immobilized in position in the long term, this being regardless of the activity performed by the patient fitted with this ventricular assist assembly.

While the rate of blood flow through the aortic valve 15 is rendered optimal because the distal end of the pump body 14 is centered on the aortic valve 15, any potential formation of a clot is also avoided.

Figure 4:
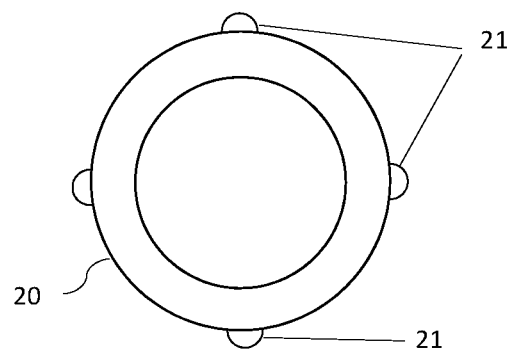
FIG. 4 is a schematic view in cross section of just the pump casing or body of a cardiac pump of a ventricular assist assembly according to another aspect of the disclosure.

FIG. 4 is a schematic view in cross section of just the pump casing or body or a cardiac pump of a ventricular assist assembly according to another embodiment of the invention.

This pump body 20 comprises a plurality of elongate-cable passageways 21 which are placed external to the pump.

Purely by way of illustration, these passageways 21 are defined for example by elongate and hollow protuberances formed on the exterior surface of the pump body.

Of course, the internal wall delimiting the orifice of the corresponding anchoring ring comprises recesses the shape of which complements these protuberances, so as to allow the cardiac pump to pass through the orifice when it is being attached to this anchoring ring.

These recesses are also configured in order, by collaboration with these protuberances, to provide the assembly of the cardiac pump with the anchoring ring the required sealing.

What is claimed is:

1. A ventricular assist assembly for assisting a heart, said assembly comprising:
    an anchoring device for anchoring a cardiac pump, which device is intended to be assembled with an opening in a ventricular wall of said heart, said anchoring device delimiting an internal passage,
    a cardiac pump intended to be attached to said anchoring device, said cardiac pump being configured for intraventricular insertion into said heart, said cardiac pump having a distal end,
    said cardiac pump extending through said internal passage into said heart when attached to said anchoring device implanted in said opening so that its distal end is placed in a ventricular chamber, and
    a stabilizing device for stabilizing said cardiac pump, comprising at least two elongate, biocompatible and flexible connecting members, each elongate connecting member being intended to connect a part of said cardiac pump that is positioned in said ventricular chamber to an internal wall of said ventricular chamber,
    wherein for each elongate connecting member, said assembly comprises an attachment element so as to anchor said connecting member in said internal wall, and wherein said attachment element is an anchoring screw axially extending said elongate connecting member and placed at the distal end thereof.

2. The assembly as claimed in claim 1, characterized in that each elongate connecting member is chosen from the group comprising an elongate cable, a filament, a chord, a rod and combinations of these elements.

3. The assembly as claimed in claim 1, characterized in that said assembly also comprises a ring or a collar intended to surround the distal end of said cardiac pump, at least some of said elongate connecting members being secured by one of their ends to this ring or, respectively, to this collar.

4. The assembly as claimed in claim 3, characterized in that, with said elongate connecting members secured to said ring or to said collar, the assembly formed by said ring or said collar and said connecting members is made from a shape memory material so that, when introduced into the chamber, this assembly transitions from a non-deployed configuration to a deployed configuration in which the free ends of the connecting members come to bear against the internal walls of said ventricular chamber.

5. The assembly as claimed in claim 1, characterized in that, with each elongate connecting member being an elongate cable or a rod, said cardiac pump comprises cable passageways configured to each allow the insertion of a corresponding elongate cable or rod, from the outside of the heart toward the inside of said ventricular chamber when said pump is attached to the anchoring device.

6. The assembly as claimed in claim 5, characterized in that the body of each elongate cable or rod is configured to exhibit torsional stiffness for transmitting along its entire length a rotational movement that is imparted from a proximal end of this cable or of this rod.

7. The assembly as claimed in claim 5, characterized in that the cable passageways extend from the proximal end of said cardiac pump as far as a part of said pump that is intended to be placed inside said chamber when said pump is attached to the anchoring device secured to said opening.

8. The assembly as claimed in claim 5, characterized in that at least part of at least one of said passageways is positioned in the thickness of the lateral wall delimiting the pump body and/or is delimited by a hollow and elongate element projecting from the pump body.

9. The assembly as claimed in claim 5, characterized in that each passageway comprises a nonreturnable valve in order to seal same.

10. The assembly as claimed in claim 1, characterized in that said pump is a propulsive cardiac pump.

\* \* \* \* \*